United States Patent [19]

Miyasaka et al.

[11] Patent Number: 4,987,032
[45] Date of Patent: Jan. 22, 1991

[54] FUNCTIONAL ORGANIC THIN FILM AND METHOD OF MANUFACTURE THEREOF

[75] Inventors: Tsutomu Miyasaka; Koichi Koyama, both of Kanagawa, Japan

[73] Assignee: Fuji Photo Film Co., Ltd., Kanagawa, Japan

[21] Appl. No.: 210,941

[22] Filed: Jun. 24, 1988

[30] Foreign Application Priority Data

Jun. 26, 1987 [JP] Japan .................................. 62-158994
Jun. 26, 1987 [JP] Japan .................................. 62-158995

[51] Int. Cl.$^5$ ............................ B32B 9/04; B05D 3/06
[52] U.S. Cl. ..................................... 428/411.1; 428/500; 428/420; 428/442; 428/459; 427/402; 427/2; 427/35; 427/54.1; 427/55; 204/157.6
[58] Field of Search ....................... 428/500, 411.1, 420

[56] References Cited

U.S. PATENT DOCUMENTS 4,597,999 7/1986 Lingwood .
4,598,056 7/1986 Barraud et al. ........................ 502/4
4,647,518 3/1987 Matsuda ................................ 430/21
4,668,584 5/1987 Uzgiris et al. ....................... 428/408

FOREIGN PATENT DOCUMENTS 82093 7/1981 Japan .
153559 7/1986 Japan .

*Primary Examiner*—P. C. Sluby
*Attorney, Agent, or Firm*—Sughrue, Mion, Zinn, Macpeak & Seas

[57] ABSTRACT

Disclosed are a functional organic thin film formed of a monolayer or multilayers composed of reactive functional group-containing amphiphilic organic molecules in which at least one of the amphiphilic organic molecules is a precursor of a nitrene or carbene and a functional organic thin film containing at least one kind of functional organic molecules formed by the reaction between the nitrene or carbene derived from the precursor and a guest compound molecule of a different kind as well as a method of producing the functional organic thin films. Utilizing the reactivity of the thin film, a functional compound, preferably a biotechnology-related functional compound, of various kinds can be fixed onto the film for use in the sensor image formation or information recording fields.

9 Claims, 3 Drawing Sheets

Glucose Oxidation on GOD-fixed Substrate
1. Substrate Fixed under Light Irradiation
2. Substrate Fxied in the Dark Glucose Oxidation on GOD-fixed Substrate
1. Substrate Fixed under Light Irradiation
2. Substrate Fxied in the Dark

FUNCTIONAL ORGANIC THIN FILM AND METHOD OF MANUFACTURE THEREOF

FIELD OF THE INVENTION

The present invention relates to an organic ultrathin film comprising reactive functional group-containing organic molecules and a method of manufacturing the film, and in particular, it relates to an organic ultrathin film which is capable of fixing a functional compound, such as a bioactive protein or the like, on the thin film by a chemical bond and in high density. The present invention also relates to a functional organic ultrathin film having such a functional compound fixed thereon and to a method of manufacturing the film.

BACKGROUND OF THE INVENTION

A monolayer and a multilayer film formed, for example, by the Langumuir Blodgett method (hereinafter referred to as "L-B method") or the like has the properties of an ultrathin film in which organic molecules are in a monodimensional orientation and are present in high density, and these are used in various fields according to their characteristic functions due to the properties.

Compounds which are suitable for formation of a monolayer are amphiphilic surfactant type molecules having both a hydrophilic group and a hydrophobic group. Such compounds are spread over the surface of an aqueous subphase from a volatile organic solution, and then pressure is applied thereto so as to compress the molecules under an appropriate surface pressure whereby the molecules are oriented such that the hydrophilic groups face downwards to the aqueous subphase surface and the hydrophobic groups face upwards from the surface and the molecules are densely packed so as to form a monolayer. Insoluble compounds wherein the whole molecule is hydrophobic cannot be oriented and therefore are easily aggregated. Such aggregation makes it difficult to impart a stable surface pressure to the molecules to form a monolayer. Accordingly, the most important factor for molecular planning of compounds for monolayer formation is to provide compounds which are well balanced in the hydrophilicity and hydrophobicity, which are insoluble in water and are nonvolatile.

As mentioned above, the molecular-oriented monolayer has particular hydrophilic groups or hydrophobic groups entirely on the surface of the layer and the groups are densely positioned on the plane face of the surface, and therefore the monolayer is characteristically and significantly different from any other cast film with no orientation. Because of the characteristics of such a monolayer, it is possible to build the monolayers one by one on a substrate having either a hydrophilic surface or a hydrophobic surface to form a multilayer film on the substrate, the thus formed multilayer film having particular hydrophilic groups or hydrophobic groups on the surface of the uppermost layer. Accordingly, when organic molecules having a hydrophilic or hydrophobic group with a particular functional groups are used, a functional organic ultrathin film can be obtained where the organic molecules are densely packed and oriented in the resulting multilayer with the functional groups facing towards the surface of the multilayer.

In general, the surface density of the molecules or functional groups in such a functional organic ultrathin film is from $10^{13}$ to $10^{15}$ molecules/cm$^2$ or so, and the film has a characteristic feature that the thickness of the film can be freely controlled within the range of a minimum of 20 Å or so.

An attempt has been made to apply a functional compound of a different kind (hereinafter referred to as a "guest compound") to the surface of such organic thin films or to insert a guest compound into the inside of the film, by virtue of a mutual reactivity of the guest compound and the hydrophilic group, hydrophobic group or functional group of the amphiphilic organic molecule of the film, so that the function of the guest compound is imparted to the thin film.

The most simple examples of such an attempt include: (1) a method where a guest compound is mixed with a monolayer-forming compound (hereinafter referred to as "host compound") in an appropriate developer solvent prior to film formation and the resulting mixture is spread over the surface of an aqueous subphase so as to form a mixed monolayer containing the host molecules, and (2) a method where a monolayer of a host compound is first coated on a substrate and then a monolayer of a guest compound is superposed thereover.

As one embodiment of such methods, for example, a study of a combination of a donor molecule and an acceptor molecule for control of the direction of transferring of electrons or energy has been reported in H. Kuhn, *Proceeding of International Symposium on Future Electron Devices*, page 1, 1985. In this case, however, since the guest compound is required to be a film-forming and hardly water-soluble compound like the host compound, the types of guest compounds that can be used are limited. In addition, when the guest compound is to be spread together with the host compound, a solvent which is compatible with both the host compound and the guest compound must necessarily be used, but the selection of such a solvent is not easy. Further, when the guest compounds are embedded into the monolayer of the host compounds to form a mixed monolayer, the resulting monolayer has a form where the guest compounds are inserted into the host molecules as a spacer, and therefore, there is a problem that the surface density of the guest molecules is limited to a low value.

As another embodiment, there is a method where guest molecules are applied to the monolayer of host molecules, which has previously been formed on the surface of an aqueous subphase or on the surface of a substrate, from a guest molecule-containing aqueous solution so that the guest molecules are attached to the surface of the monolayer or are inserted into the monolayer due to diffusion, adsorption or complex formation.

In this method, the adsorption of or complex formation with the guest molecules is generally accelerated by the hydrophobic bonding force or electrostatic attractive force between the molecules so that the adsorption and complex formation may become the equilibrated state. Utilizing this method, Fromherz et al. disclosed a process of applying guest molecules of bioactive proteins such as enzymes or the like to a host monolayer of fatty acids or esters by adsorption or insertion (*FEBS Letters*, Vol. 49, page 329, 1975).

In addition, also utilizing this method, another example where a monolayer to which a biological protein has been adsorbed is coated on a substrate by the L-B method is described in Japanese Patent Application (OPI) No. 251930/85 (FR-8407213) (the term "OPI" as used herein refers to a "published unexamined Japanese Pat. application"). However, since the monolayer formed by applying functional guest molecules to the layer by the adsorption method or complex formation method occurs via the chemical equilibrium of the adsorption or complex formation of the guest molecules, there is a problem in that the guest molecules are released from the monolayer by washing or similar mechanical action. Such a problem is a serious defect to practical use when a chemical reaction is to be conducted on the monolayer by way of the function of the guest molecules because the guest molecules peel away from the monolayer during the reaction and the function of the monolayer is lowered. In addition, in this embodiment, the functional groups of the guest molecules become oriented at random on the surface of the monolayer or they get embedded between the host molecules, and as a result, there is still another problem in that the function of the guest molecules can not be fully used.

Moreover, in accordance with this method, since the guest compounds indiscriminately adsorb to the surface of the thin film, it is impossible to control the part of the film to which the guest compounds are to be applied. This is a great problem in the case where the functional thin film is to be applied to a limited part of a small substrate such as a sensor or the like or in the case where the thin film is to be fixed as a pattern.

SUMMARY OF THE INVENTION

Accordingly, the first object of the present invention is to provide a reactive monolayer or multilayer capable of highly densely fixing functional guest molecules to the surface of the thin film due to the chemical bond between the molecules and the film and in particular to provide a monolayer or multilayer having reactive functional groups, which are helpful for the bonding reaction with the guest molecules, on the surface of the film which are highly densely and uniformly distributed.

The second object of the present invention is to provide a functional organic thin film in which water-soluble functional guest compounds are highly densely bonded to the surface of a reactive monolayer or multilayer by a chemical bond therebetween.

The third object of the present invention is to provide a method of highly densely fixing functional guest molecules to the surface of a reactive organic thin film by forming chemical bonds between the molecules and the film.

The fourth object of the present invention is to provide a method of forming a functional thin film pattern by fixing functional guest molecules to a limited part on the thin film by light irradiation by way of a photochemical reaction of the functional guest molecules.

The fifth object of the present invention is to provide a method of forming a functional thin film having a stable and highly effective function by photo-fixation.

These and other objects of the present invention can be attained by providing a functional organic thin film formed of a monolayer or multilayers comprising amphiphilic organic molecules, in which at least one of the amphiphilic organic molecules is a precursor of nitrene or carbene.

The above objects of the present invention can also be attained by providing a functional organic thin film containing at least one kind of functional organic molecules formed by the reaction between the nitrene or carbene derived from the precursor and a molecule of a different kind (guest compound).

The present invention also provides a method of making a functional organic thin film formed of a monolayer or multilayers at least partly having amphiphilic organic molecules which have a bonding reactive group or a precursor of a bonding reactive group, the method comprising exposing the monolayer or multilayers to light in the presence of a guest compound whereby the guest compound is chemically bonded to the monolayer or multilayers.

DETAILED DESCRIPTION OF THE INVENTION

Figure 1:
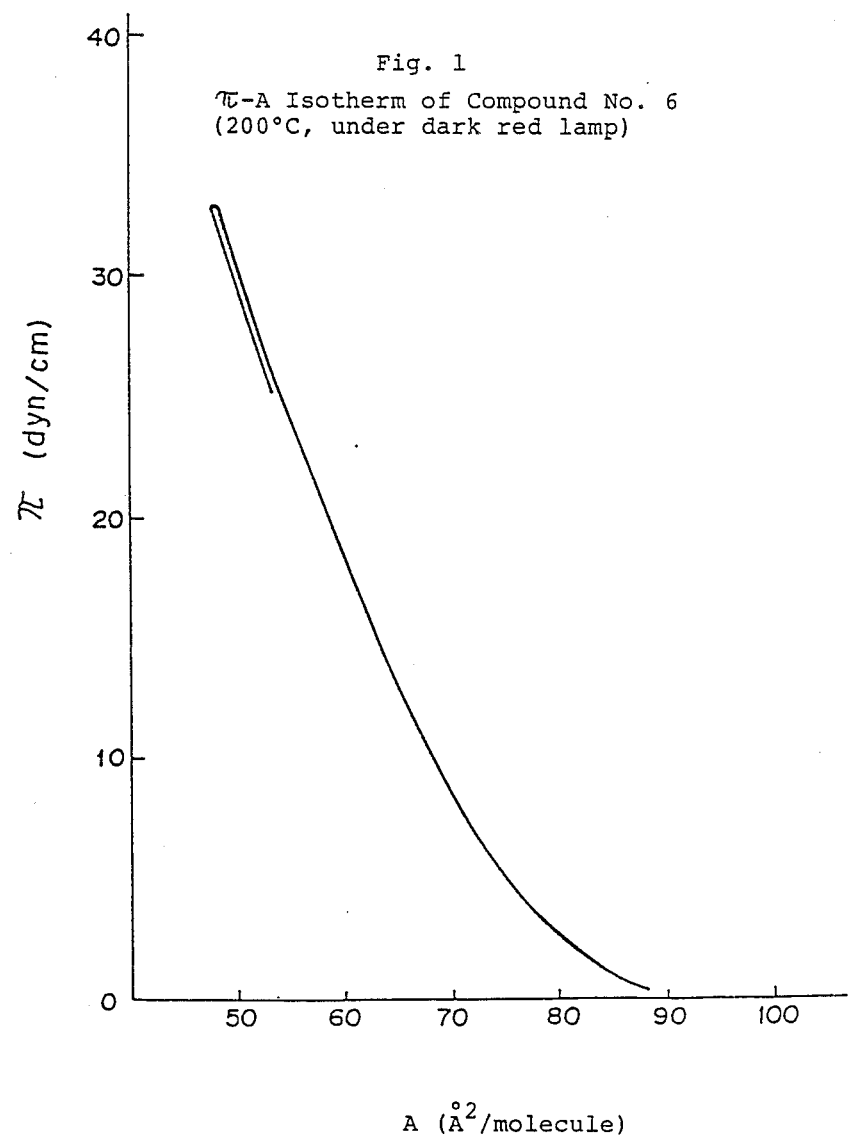
FIG. 1 is a graph of the $\pi$-A isotherm of Compound No. 6 used in Example 1.

An amphiphilic compound comprising the amphiphilic molecules (host compound) to be used in the present invention as a reactive compound for formation of the monolayer or multilayers has at least one precursor of a nitrene or carbene in the molecule as a functional group which is reactive to bond reaction. The host compound may form a stable monolayer on the surface of an aqueous subphase, either alone or together with any other amphiphilic compound.

Especially useful host compounds include amphiphilic compounds having an azido group as an organic group that is a precursor of a nitrene, and amphiphilic compounds having an $\alpha$-diazoketone group or an aryl-diaziridine group as a precursor of a carbene. These compounds undergo an $N_2$-removing reaction under heat or light to form a nitrene or carbene. The $N_2$-removing reaction is accelerated especially by irradiation with light having a wavelength range which is adsorbed by the compounds. This is described, for example, in H. Bayley & J. R. Knowels, *Methods for Enzymology*, Vol. 46, pages 69 to 114 (1977), which relates to a photo-affinitive labeling method using compounds as described above.

The host compounds for use in the present invention can contain any other reactive group(s), for example, polymerization reactive groups (e.g., unsaturated bond, etc.) or the like, in the molecule.

Preferred examples of the host compounds for use in the present invention are shown below, which, however, are not intended to restrict the scope of the present invention.

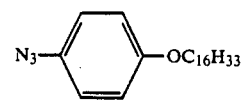

1.

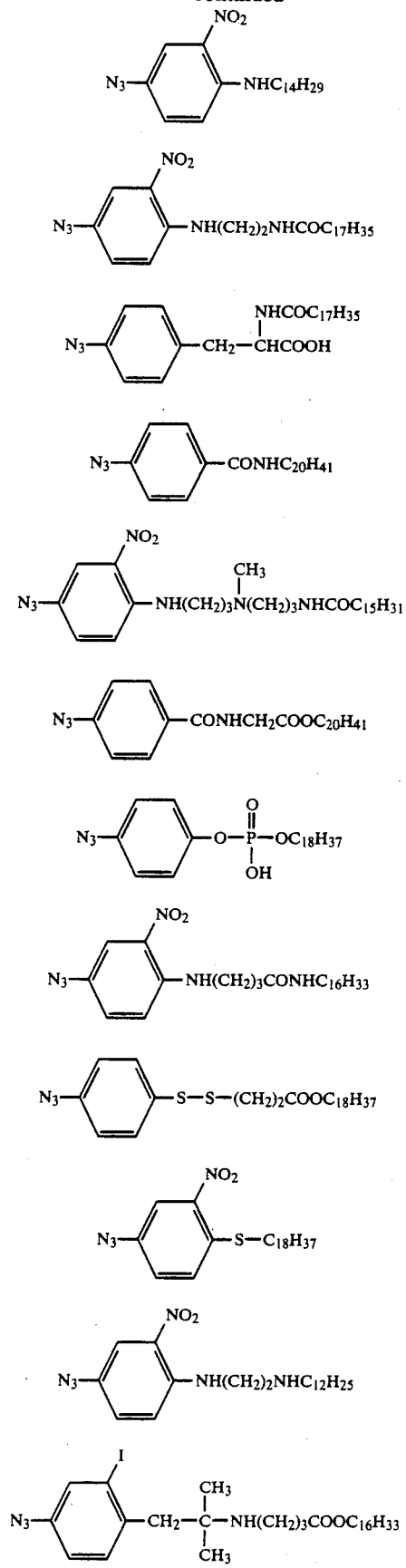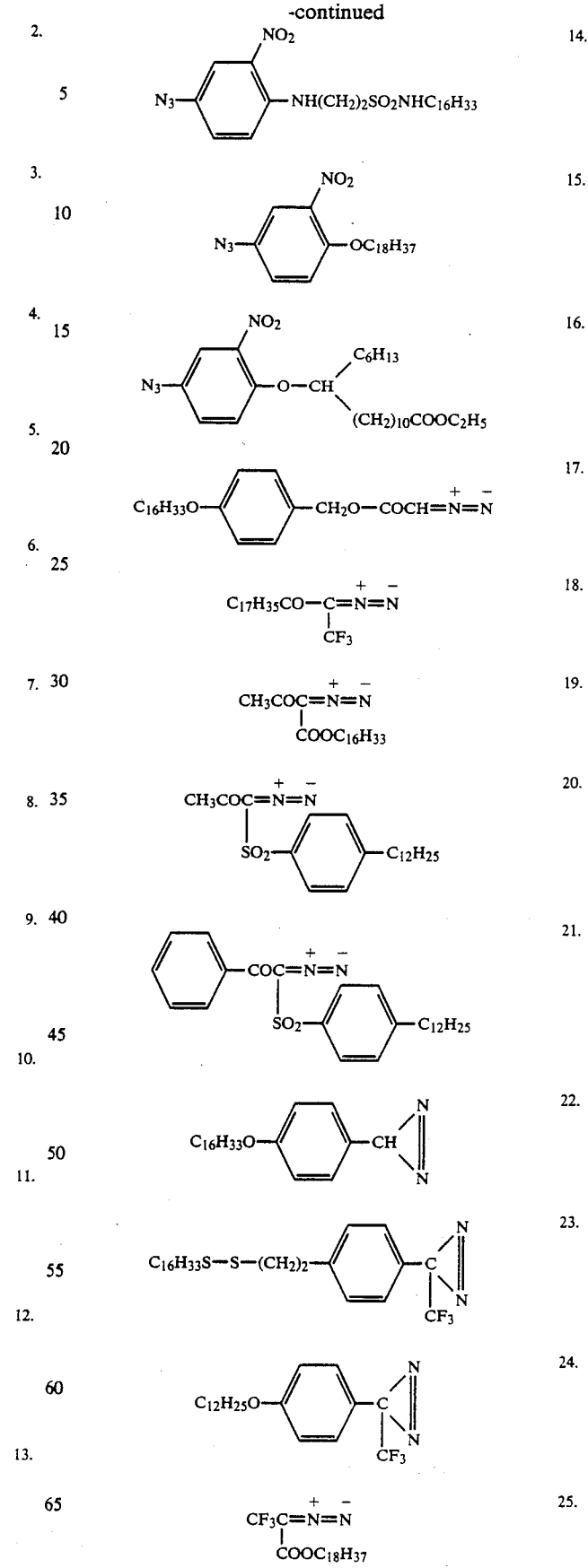

-continued
26. 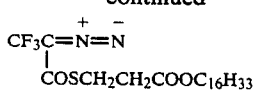
27. 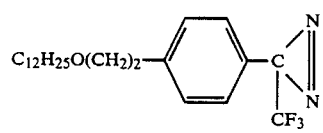
28. 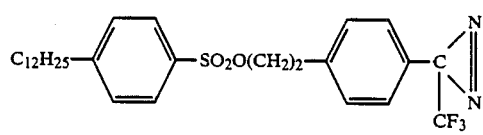
29. 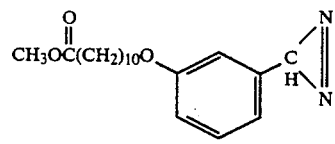
30. 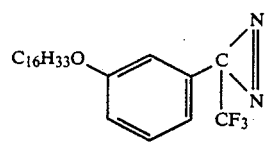
31. 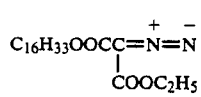
32. 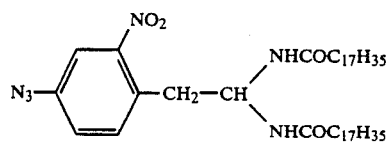
33. 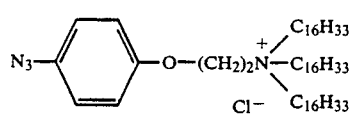
34. 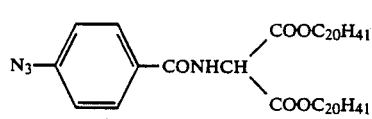
35. 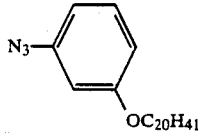
36. 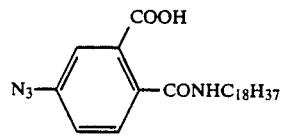
37. 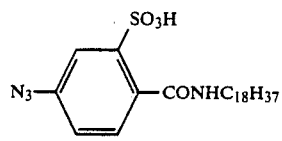
-continued
38. 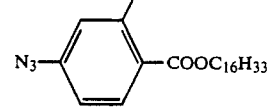
39. 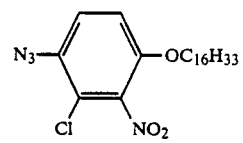
40. 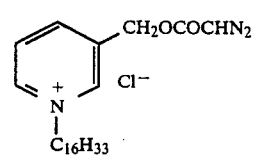
41. 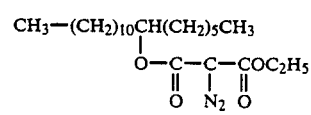
42. 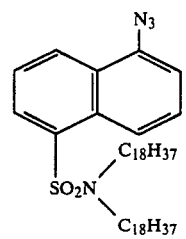
43. 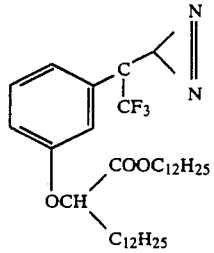
44. 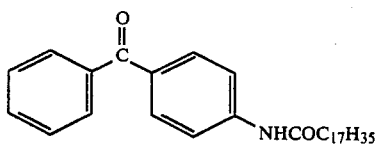
45. 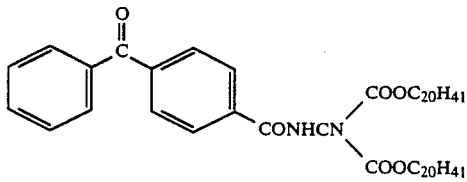
46. 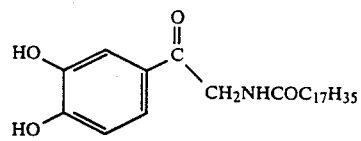

47. 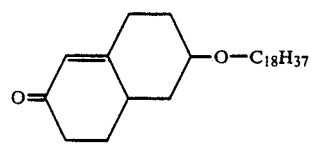

48. 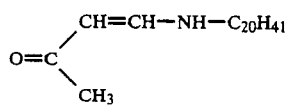

49. 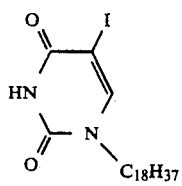

50. 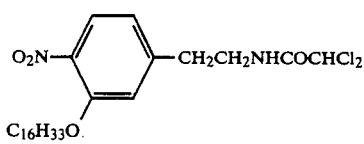

51. 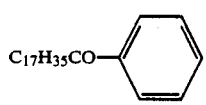

52. 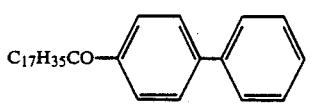

53. 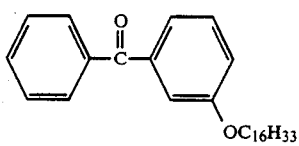

47. 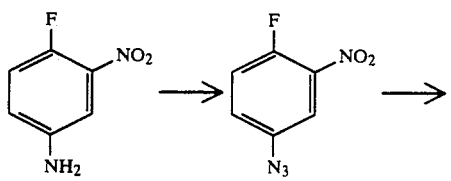

48. 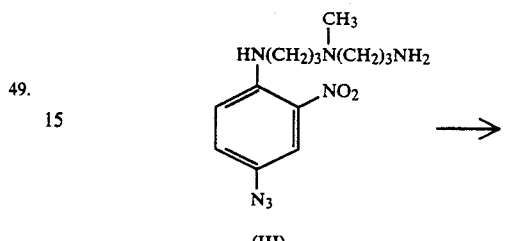

49. (III)

50. 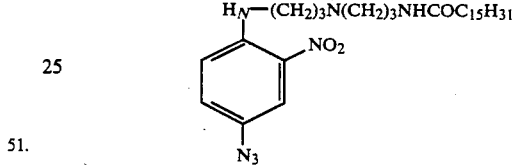

51. 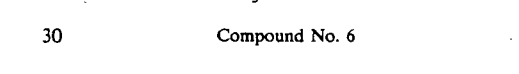

Compound No. 6

The host compounds for use in the present invention can be produced easily by conventional organochemical means. For instance, in the case of nitrene precursors, an aromatic amine is diazotized and then processed with sodium azide to form an aromatic azide compound with ease. For introduction of a hydrophobic group into the compounds, an aromatic substitution reaction with an alkylamine or an amide forming reaction as well as an etherification reaction with an alkyl halide can be utilized for producing the intended hydrophobic compounds.

A synthesis example for illustrating the production of a typical compound of the present invention is set forth below.

SYNTHESIS EXAMPLE

The above-mentioned compound No. 6 was produced in accordance with the following reaction formula:

Production of Intermediate (II)

10 g of 4-fluoro-3-nitroaniline (I) was dissolved in 100 ml of concentrated hydrochloric acid while hot. The resulting solution was cooled to −15° to −20° C., and a solution of 4.8 g of sodium nitrite dissolved in 10 ml of water was gradually dropwise added thereto at −15° C. or lower. Further, a solution of 4.4 g of sodium azide dissolved in 16 ml of water was gradually added thereto at −15° C. or lower. After the addition, the whole was stirred for about 30 minutes and when the generation of nitrogen gas from the reaction system completely ceased, the crystals formed were removed by filtration, washed well with cold water and then dried with air. Yield: 9.8 g.

Production of Intermediate (III)

A solution of 5.5 g of the intermediate (II) obtained in the above-mentioned step, dissolved in 50 ml of ether, was stirred with a magnetic stirrer. On the other hand, a mixture solution was prepared by adding 18 m( of N-(3-aminopropyl)-N-methyl-1,3-propanediamine to 100 ml of ether, and this was added to the previously prepared solution and then stirred for about 1 hour at room temperature. The reaction was followed by silica gel chromatography. After the completion of the reaction, 200 ml of water was added to the reaction mixture, which was then extracted twice with ethyl acetate. The ethyl acetate layer was washed with water. This was dried with magnesium sulfate and the solvent was evaporated out under reduced pressure. The residue thus obtained was directly used in the next step without being further purified.

Production of Compound No. 6

0.9 g of the oily residue obtained in the previous step was dissolved in 30 ml of chloroform, and then 0.8 ml of triethylamine and 0.8 g of palmitoyl chloride were added and the mixture was stirred for about 30 minutes. 50 ml of dilute hydrochloric acid was added to the reaction solution, which was then extracted with chloroform. The chloroform layer was dried with magnesium sulfate and then the solvent was evaporated out. The residue was purified by silica gel chromatography (chloroform/methanol=20/1 by volume), to obtain the intended Compound No. 6 as a single spot. Yield: 1.1 g.

Most of the other compounds can be produced in accordance with the above-mentioned process, and, as mentioned above, all of the compounds can be made by some conventional means.

The developer solvent for monolayer formation in the present invention includes conventional volatile nonpolar organic solvents such as chloroform, dichloromethane, benzene, toluene, ether and the like, as well as a mixture comprising the organic solvent and a polar hydrophilic solvent such as alcohols, water, etc.

The aqueous subphase to be used in the present invention for monolayer formation may be selected from various pH buffers as well as various solutions of salts of metals such as calcium, barium, cadmium, potassium, sodium, etc. If desired, the temperature of the aqueous subphase may be controlled to be a low temperature or a high temperature. Further, the subphase can be agitated by stirring or can be vibrated, so that the molecules that are to constitute the monolayer may be reacted with the compounds in the aqueous subphase, if desired. In the manufacture of the monolayer, the gaseous atmosphere on the aqueous subphase may be substituted by an inert gas such as $N_2$, Ar or the like, so that the resulting monolayer may be prevented from being oxidized or aged.

It is preferred that the aqueous subphase on which the host compound monolayer is to be developed in accordance with the method of the present invention have a pH value that falls within the range of from 4 to 10.

In addition, it is also preferred that the monolayer be processed in a dark room or under a dark red light throughout the steps of development, compression and multiplication.

For chemical bonding of water-soluble functional guest compounds of a different kind to the monolayer or multilayer of host compounds, in accordance with the present invention, various means can be employed.

For instance, there is a method in which guest compounds are added to the aqueous subphase for the host compound monolayer previously formed on the surface of the subphase, or alternatively, a monolayer is transferred to a second aqueous subphase containing guest compounds dissolved therein, whereby the host compounds in the monolayer are reacted with the guest compounds in the aqueous interface by a bonding reaction. In this case, the concentration of the guest compounds in the aqueous subphase is preferably from $10^{-6}$ to $10^{-3}$ M. The surface pressure of the monolayer in the bonding reaction can be varied throughout the reaction step. For example, the surface pressure can be kept low during the reaction, if desired, and the pressure can be elevated after the reaction for recompression of the layer formed, and the procedure is often advantageously employed for the purpose of elevating the reaction efficiency.

As another embodiment, there is a method in which a solid substrate which has already been coated with a monolayer or multilayer comprising host compounds is dipped in an aqueous solution containing guest compounds so that the guest compounds are reacted with the host compounds in the solid-liquid interface.

As still another embodiment, there is a method in which a monolayer comprising guest compounds is formed and this is overcoated on a multilayer of host compounds which has previously been formed on a substrate, and then light is irradiated on the multilayer so that the compounds react with each other in the solid-solid interface by a bonding reaction.

In the present invention, the above-mentioned methods can properly be selected and used in accordance with the kinds of host compounds and guest compounds. Most preferably, the second-mentioned method where the reaction is conducted in the solid-liquid interface is advantageous for the present invention.

In the process of the present invention where the guest compounds are reacted with the host compounds in the monolayer or multilayer by chemical bonding, it is preferred that light or heat be imparted to the layer, and in particular, light irradiation is especially preferred. By the light irradiation, the $N_2$-removing reaction can be accelerated so that the resulting active nitrogen can attack the guest compounds to form the chemical bond between the thus attacked guest compounds and the host compounds.

In this case, ultraviolet rays or visible rays can be used for the purpose of light irradiation. Preferred is a method where a visible ray which is almost not harmful to guest compounds is irradiated on the film of host compounds which have an absorption in the range of the visible ray (for example, nitrobenzene derivatives, etc.).

When the layer is heated, the time of heating may be simultaneous with light irradiation or may be before or after the light irradiation.

In accordance with the present invention, when guest compounds are reacted with a host monolayer on the aqueous subphase by chemical reaction or when a monolayer is coated on a substrate prior to the chemical reaction, the surface pressure of the film can be any desired value, but the preferred surface pressure is within the range which is lower than the molecule-disintegrating pressure in the isotherm between monolayer surface pressure $\pi$ (dyne/cm) and the molecule-occupying area ($A^2$/molecule) and which is sufficiently higher than the critical pressure for beginning the surface pressure raising, or that is within the range where the molecules may be sufficiently oriented.

The substrate which carries a monolayer or multilayer containing a precursor of nitrene or carbene, in the present invention, is preferably photochemically inactive on the surface with which the monolayer or multilayer is contacted, for the purpose of not interfering with the reaction between the precursor and a guest compound. The term "photochemically inactive" as herein referred to means that the substrate is free from any chemical change including radical formation, decomposition and polymerization and is stable to visible ray or ultraviolet ray irradiation. Such photochemically inactive substrates include, in general, inorganic substances such as metals, semiconductors, insulating materials, etc. Although the surface of the substrate is preferred to be photochemically inactive, this may be active to any other stimulations than light (such as heat, pH, etc.).

Various multiplication methods including the L-B method can be employed for coating the monolayer formed on the surface of an aqueous subphase onto the surface of a substrate or support. The L-B method which is a vertical adhesion method is described, for example, in *Journal of American Chemical Society*, Vol. 57, page 1007 (1935); G. L. Gains, Jr., *Insoluble Monolayers at Liquid-Gas Interfaces* (Interscience, New York, 1966); S. Fukuda, *Material Techniques*, Vol. 4, page 261 (1986), etc. As a coating means, other various methods than the L-B method, for example, a horizontal adhesion method or a rotary adhesion method, can be employed. (For example, refer to Japanese Pat. Application (OPI) Nos. 189929/85 and 42394/86.) A multilayer can be formed by repeating the operation of coating the monolayer onto the substrate. A continuous multiplication method, for example, as described in Japanese Pat. Application (OPI) No. 209245/85 can also be employed. In this case, it is preferred that at least a part of the host compounds of the present invention is incorporated into the outermost monomolecular layer, and the other monomolecular layers which are nearer to the substrate than the outermost layer may be composed of other amphiphilic organic molecules (surfactant type molecules).

In the step of forming monolayers and multi-layers, electromagnetic radiation can be irradiated on the monolayer and aqueous subphase so that the chemical reaction in the monolayer can be accelerated. The electromagnetic radiation for this purpose includes ultraviolet rays, visible rays, infrared rays, and microwaves as well as other radiations such as X-rays, $\beta$-rays, $\gamma$-rays, etc.

The monolayer forming compounds for constituting the organic thin film of the present invention may have chemical bonds between molecules of the same kind or may be polymerized by intermolecular polymerization. Intermolecular chemical bonds of this kind can be introduced into the monolayer which is formed on the surface of an aqueous subphase by heat or by irradiation with electromagnetic radiation, or alternatively, after monolayers have been multiplied on a substrate to form multilayers, the chemical bond can be introduced into the thus formed multilayers in the same manner.

As the support (substrate) to be used in the present invention for forming a monolayer or multilayers in accordance with the L-B method, various kinds of materials can be used, for example, conductors such as various metals, inorganic glass materials (glass, quartz, etc.) and other inorganic insulating materials, various kinds of inorganic and organic crystals, inorganic semiconductors ($SnO_2$, $In_2O_3$, $ZnO$, $TiO_2$, $WO_3$, $GaAs$, $Si$, etc.), organic semiconductors, organic conductors, organic polymers as well as complex materials of the above-mentioned materials, etc. The material may be a transducer, such as an electrode or sensor, which can be connected with the outer electric circuit. The surface of the material can be processed by various physical or chemical treatment so as to be hydrophilic or hydrophobic. As one preferred embodiment for hydrophobic treatment, a method can be mentioned in which an alkylsilane derivative as a coupling agent is reacted with the surface of the substrate.

In the constitution of the thin film material of the present invention, the surface of the substrate or support material can be chemically fixed with the molecules which constitute an organic multilayer to be contacted with the surface of the substrate or support material. Fixation of this kind can be attained by acceleration of the chemical bonds between the reactive groups (e.g., a hydroxyl group, etc.) in the surface of the substrate and the terminal reactive groups (e.g., active silane, azide, etc.) in the multilayer molecules by way of thermal stimulation or electromagnetic ray irradiation.

As the guest compounds to be bonded to the monolayer of reactive host compounds, in accordance with the present invention, there may be mentioned various functional organic compounds and organic metal compounds. These include, for example, synthetic substances such as dyes, fluorescent dyes, redox compounds, electroconductive compounds, optically active substances, inclusion compounds, catalysts, various functional polymers, etc., as well as physiologically active natural substances such as enzymes, proteins, antigens, antibodies, etc. Preferred among these are water-soluble functional compounds. Examples of especially preferred substances are biotechnology-related substances such as enzymes, antigens, antibodies, etc. In particular, enzymes are most preferred as these can be bonded to the organic thin film of the present invention with high efficiency.

Examples of enzymes which can be advantageously employed in the present invention include oxidases such as glucose oxidase, cholesterol oxidase, urikase, choline oxidase, etc.; dehydrogenases such as alcohol dehydrogenase, glycerol dehydrogenase, glucose-6-phosphate dehydrogenase, glutamic acid dehydrogenase, etc.; as well as peroxidase, uriase, riboprotein lipase, diaphorase, catalase, various kinases, cholesterol esterase and other analytical enzymes.

As the guest compounds of antigens or antibodies, there are many substances containing immunoglobulin G, etc., and these are summarized, for example, in Y. Yamamura, *Study of Immunity* (published by Dobun Publishing Co., Japan, 1986).

Any desired functional compound, such as an enzyme, a protein or the like, can be chemically fixed on the surface of the thin film of the present invention because of the reactivity of the surface of the film, and after the fixation, the highly efficient chemical reaction (catalyst reaction, photochemical reaction, oxidation reduction, etc.) of the functional compound or physical variation thereof (optical variation, electric variation, etc.) can be utilized in various fields of sensor image formation, information recording, energy change, etc. Accordingly, the present invention is extremely industrially advantageous.

The following examples are intended to illustrate the present invention but not to limit it in any way.

Unless otherwise specified, all percents, ratios, etc., are by weight.

EXAMPLE 1

Figure 2:
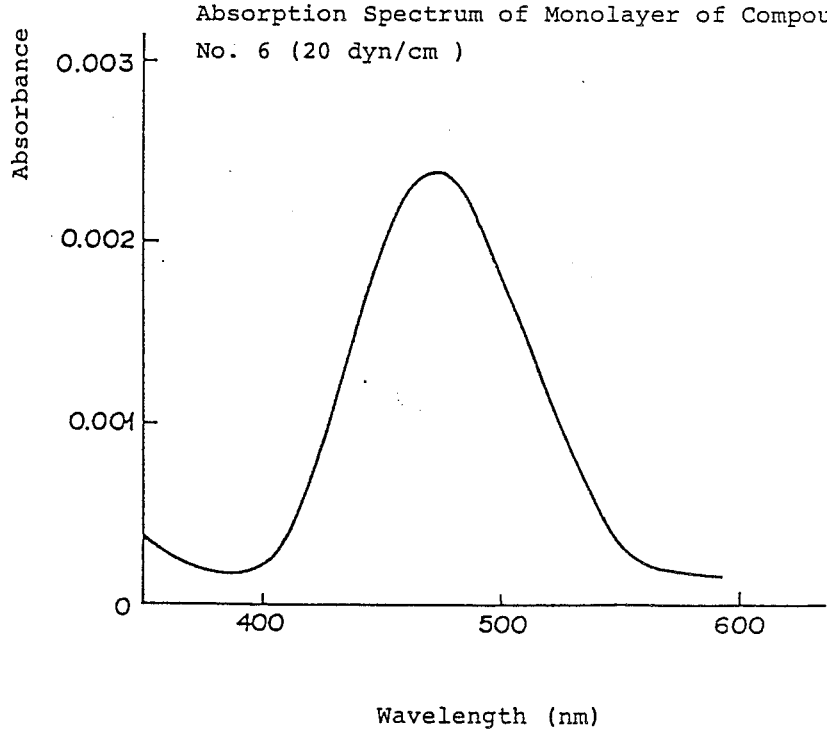
FIG. 2 is a graph of the absorption spectrum of the monolayer of Compound No. 6 of Example 1.

The aforesaid amphiphilic compound (No. 6) having a reactive azido group was dissolved in dichloromethane to form a $10^{-3}$ M solution, and 50 $\mu$l of the solution was spread over a $10^{-3}$ M neutral phosphate buffer in a monolayer-forming water tank ($20 \times 40 \times 7$ cm) under a red lamp to form a monolayer. The monolayer thus formed was compressed by way of an automatic compression control device at a constant rate of 40 cm$^2$/min at 20° C., and as a result the good $\pi$-A isotherm between the molecule-occupying area (A) and the surface pressure ($\pi$) as shown in FIG. 1 was obtained. The $\pi$-A isotherm could be reversibly reproduced even to the pressure-recovering (reducing) direction, and the monolayer formed was ascertained to have a cyclically stable characteristic. Next, the absorption spectrum of the monolayer on the aqueous subphase was measured by the use of a multiphotometer (manufactured by Otsuka Electronics Co.) at a surface pressure of 20 dyne/cm, and as a result the spectrum as shown in FIG. 2, which had a visible absorption peak at 470 nm, was obtained.

The reactive azido compound monolayer thus produced was multiplied on a substrate as mentioned below. A glass substrate was surface-treated with a 10% toluene solution containing trimethylsilane chloride so that the surface was silanoated and the substrate was made hydrophobic. While the surface pressure of the monolayer was kept at 20 dyne/cm, the substrate was adhered to the surface of the aqueous subphase in parallel therewith and then the substrate was immediately drawn up. Thus, the monolayer was transferred to the substrate to cover the surface thereof. The same operation was repeated three times, so that three monolayers were multiplied on the substrate. The deposition ratio was 1.0. The absorption spectrum of the multilayer thus formed was measured, and as a result a broad spectrum which was similar to that of the monolayer of FIG. 2 was obtained. From this it was ascertained that the surface of the substrate carried the azido compounds.

EXAMPLE 2

In the same manner as in Example 1 except that the aforesaid Compound No. 3 was used as the azido compound, a monolayer comprising Compound No. 3 was deposited two times on a glass substrate (2.6×2.6 cm) at a surface pressure of 20 dyne/cm, The procedure up to the formation of the two-layer film was all carried out at room temperature in a dark room. Next, the thus formed multilayer substrate was dipped in 100 cc of a neutral phosphate buffer solution containing 15 mg of glucose oxidase (GOD) for 30 minutes while the substrate was exposed to visible light from a 100 W projector lamp for 10 minutes. On the other hand, the same operation was repeated without exposure to the light. Then the substrate was taken out from the enzyme solution and fully washed with a 1 M NaCl solution and pure water with stirring. Then the thus processed substrate was dipped in 100 cc of a neutral aqueous solution containing 0.01 M glucose as a substrate and stirred at 25° C. to conduct a glucose oxidation reaction. During the reaction, 5 cc of the reaction solution was sampled and a mixture of a leuco dye (ABTS) and peroxidase (POD), which is a color reagent, was added thereto, and as a result the dye coloration was admitted which shows the formation of hydrogen peroxide (as derived from oxidation of glucose).

Figure 3:
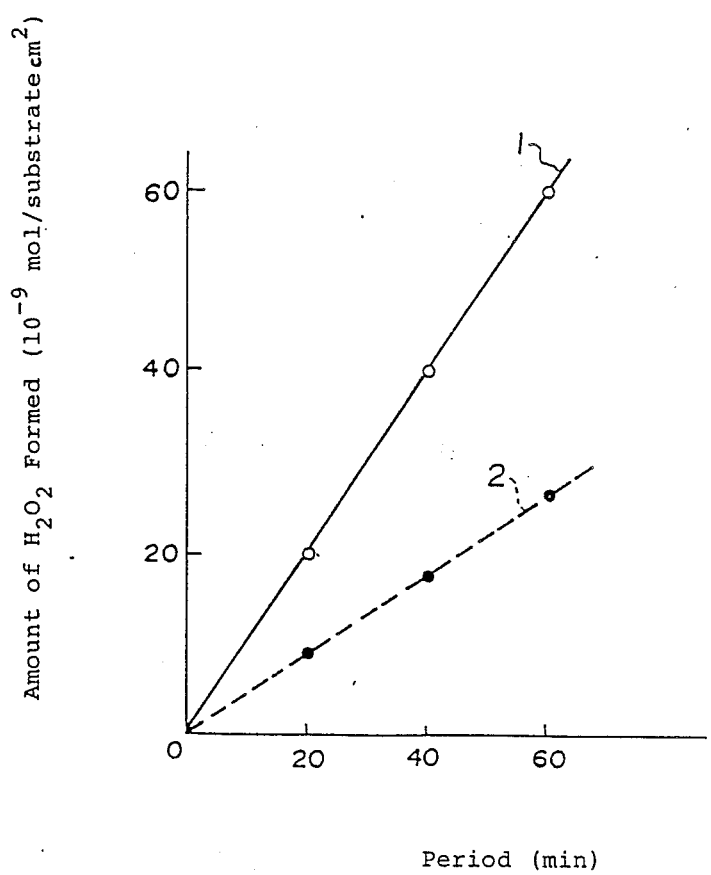
FIG. 3 is a graph showing the variation of the glucose-oxidation reaction with a lapse of time described in Example 2. The solid line represents the case where the substrate formed by reaction of multilayers and glucose oxidase under light irradiation being applied to the glucose-oxidation reaction, and the dotted line represents the case where the substrate formed by reaction of multilayers and glucose oxidase without light irradiation being applied to the glucose-oxidation reaction.

On the basis of the absorbance of the thus colored leuco dye, the amount of hydrogen peroxide formed by the enzyme reaction was determined, and as a result the linear increase of the amount of the hydrogen peroxide formed with the lapse of time, as shown in FIG. 3, was ascertained. Also, in the case where the GOD application was conducted in the absence of light irradiation, it was ascertained that glucose oxidation occurred on the multilayer substrate.

The glucose oxidation rate as obtained from the amount of the hydrogen peroxide formed and the area of the substrate as the reaction amount per cm$^2$ of the multilayer surface area was $1 \times 10^{-9}$ mol/min, in the case where the GOD application was conducted in the presence of light irradiation. The rate was sufficiently larger than the oxidation rate for the sample which had been prepared by applying GOD to the multilayer in the dark in the absence of light irradiation.

The same extreme activity in glucose oxidation was also obtained in the experiments using Compound Nos. 5, 9, 11, 17, 18 or 34, in place of Compound No. 3, as a guest compound.

EXAMPLE 3

In the same manner as in Example 2, except that the aforesaid Compound No. 30 was used as a carbene precursor in place of Compound No. 3 and that a polyethylene film was used as a substrate for multilayer formation in place of the glass substrate, a 5-layer film was formed on the polymer film by a horizontal adhesion method. The substrate with the multilayer was dipped in a GOD solution for 30 minutes, while the substrate was exposed to 313 mm light from a high pressure mercury lamp for GOD-fixation on the film.

The thus GOD-fixed substrate was rinsed with 0.1 M NaCl and pure water and then dipped in an aqueous 0.01 M glucose solution. The oxidation reaction activity by the enzyme was determined by the use of a leuco dye and POD.

Like the case of Example 2, the formation of hydrogen peroxide due to the oxidation of glucose occurred in proportion to the lapse of time, and the enzyme activity was ensured. The reaction rate of this system was sufficiently higher than the system where the GOD application to the substrate had been conducted in the absence of light irradiation.

EXAMPLE 4

The aforesaid amphiphilic compound (No. 3), which is a nitrene precursor, was dissolved in chloroform to form a $10^{-3}$ M solution, and this was spread over a $10^{-3}$ M neutral phosphate buffer solution in a monolayer-forming water tank under a red lamp to form a monolayer. After the surface pressure of the monolayer was compressed to 20 dyne/cm, the GOD was injected into the aqueous subphase with an injector so that the GOD concentration in the subphase was made to be $10^{-6}$ M. The monolayer was kept like this for 10 minutes, and then light from a 100 W halogen lamp was irradiated on the aqueous subphase for 10 minutes. In order to transfer the monolayer to a substrate, a glass substrate whose surface had been made hydrophobic by surface treatment with a trimethylsilyl chloride solution was gently adhered to the monolayer on the aqueous subphase in parallel therewith and then the substrate was immediately drawn up (by a so-called horizontal adhesion method). Thus, the monolayer was transferred to the substrate to cover the surface thereof. The deposition ratio by the coating was 1.0. After the substrate was washed with water and dried, the reflective absorption spectrum of the substrate was measured by the use of a multiphotometer (manufactured by Otsuka Electronics Co.). The visible absorption derived from the flavin in GOD was found at 400 nm or below, in addition to the broad visible absorption (620 nm or below) caused by the photodecomposition product of Compound No. 3, as compared with the sample prepared in the absence of GOD. From this it was ascertained that GOD was fixed on the film. The absorption by GOD did not lower even after the substrate was washed with water for several hours and the GOD on the substrate did not peel off.

Next, the substrate having GOD photo-fixed thereto was dipped in a 0.01 M glucose-containing buffer (pH 5.6) and reacted for 30 minutes at 25° C. A small amount of the reaction solution was sampled and a color reagent containing a leuco dye (ABTS) and peroxidase was added thereto. As a result, the color reaction to indicate the formation of $H_2O_2$ occurred, and the oxidation of glucose was ensured from the formation of $H_2O_2$. The glucose oxidation rate per unit film area was about $1\times10^{-9}$ mol/min·cm$^2$, as calculated from the amount of $H_2O_2$ formed and the film area.

For comparison, the same fixation test was carried out where methyl stearate having no reactive group was used for formation of the monolayer in place of Compound No. 3 and GOD was used as the guest compound. As a result, only a slight absorption to show the characteristic of the GOD fixation was found and the enzyme reaction activity in the glucose oxidation was about 1/10 of the above-mentioned case where the active group-containing Compound No. 3 was used.

EXAMPLE 5 as in Example 1 except that Compound No. 32 was used in place of Compound No. 3 and the GOD photofixation method was replaced by the method described below, a GOD-fixed substrate was formed. For GOD-fixation, a monolayer of Compound No. 32 was compressed to 20 dyne/cm, and then the monolayer was transferred to the surface of a hydrophobic processed glass substrate by a horizontal adhesion method so that the surface of the substrate was covered with the monolayer. The operation was conducted under irradiation of a dark red lamp. Next, the monolayer-coated substrate was dipped in an aqueous neutral $10^{-5}$ M GOD buffer solution for 10 minutes and then exposed to visible light from a 100 W halogen lamp for 20 minutes. The substrate thus GOD-fixed by photofixation was fully washed with water and then dipped in an aqueous 0.01 M glucose solution for the glucose oxidation reaction. The generation of $H_2O_2$ was detected by the use of a color reagent containing ABTS and POD, and the efficient glucose oxidation reaction was ascertained, as in the case of Example 1.

While the invention has been described in detail and with reference to specific embodiments thereof, it will be apparent to one skilled in the art that various changes and modifications can be made therein without departing from the spirit and scope thereof.

What is claimed is:

1. A functional organic thin film formed of a monolayer or multilayers comprising amphiphilic organic molecules having a hydrophobic group containing at least 12 carbon atoms, in which at least one of the amphiphilic organic molecules is a precursor of a nitrene or carbene.

2. A functional organic thin film as in claim 1, wherein the monolayer or multilayers comprising amphiphilic organic molecules containing a precursor of a nitrene or carbene is coated over a photochemically inactive solid substrate.

3. A functional organic thin film as in claim 1, wherein the monolayer or multilayers contain at least one functional organic molecule formed by a reaction between a nitrene or carbene derived from the precursor and a guest compound.

4. A functional organic thin film as in claim 1 or 2, wherein the precursor of a nitrene or carbene forms a nitrene or carbene by light irradiation of the monolayer or multilayers.

5. A functional organic thin film as in claim 3, wherein the guest compound which is to react with a nitrene or carbene derived from the precursor is a biotechnology-related compound.

6. A functional organic thin film as in claim 1, wherein said at least one amphiphilic organic molecule is an amphiphilic molecule having an azido group as an organic group that is a precursor of nitrene or an amphiphilic molecule having an α-diazo ketone group or an aryldiaziridine group as a precursor of a carbene.

7. A functional thin film having functional guest molecules fixed thereto in the form of a pattern formed by a process comprising:
    (a) forming a thin film of a monolayer or multilayers at least partially having amphiphilic organic molecules which have a bonding reactive group or a precursor of a bonding reactive group; and
    (b) image-wise exposing the monolayer or multilayers to light in the presence of a guest compound whereby the guest compound is chemically image-wise bonded to the monolayer or multilayers by way of a photochemical reaction of the functional guest molecules.

8. A functional organic thin film as in claim 7, wherein the precursor of the bonding reactive group is a molecule that forms a nitrene or carbene upon light irradiation thereof.

9. A functional organic thin film as in claim 7, wherein the guest compound is a water-soluble biological compound.

* * * * *